(12) United States Patent
Morrisroe et al.

(10) Patent No.: US 7,106,438 B2
(45) Date of Patent: Sep. 12, 2006

(54) ICP-OES AND ICP-MS INDUCTION CURRENT

(75) Inventors: Peter J. Morrisroe, New Milford, CT (US); Thomas Myles, Fairfield, CT (US)

(73) Assignee: PerkinElmer LAS, Inc., Boston, MA (US)

( * ) Notice: Subject to any disclaimer, the term of this patent is extended or adjusted under 35 U.S.C. 154(b) by 243 days.

(21) Appl. No.: 10/730,779

(22) Filed: Dec. 9, 2003

(65) Prior Publication Data

US 2004/0169855 A1  Sep. 2, 2004

Related U.S. Application Data

(60) Provisional application No. 60/432,963, filed on Dec. 12, 2002.

(51) Int. Cl.
*G01J 3/30* (2006.01)
*G01N 21/73* (2006.01)

(52) U.S. Cl. .......... 356/316; 250/288
(58) Field of Classification Search ........ 356/316; 250/288
See application file for complete search history.

(56) References Cited

U.S. PATENT DOCUMENTS

| 4,540,884 A | 9/1985 | Stafford et al. |
|---|---|---|
| 4,629,940 A | 12/1986 | Gagne et al. |
| 4,766,287 A | 8/1988 | Morrisroe et al. |
| 4,818,916 A | 4/1989 | Morrisroe |
| 5,526,110 A | 6/1996 | Braymen |
| 5,534,998 A | 7/1996 | Eastgate et al. |
| 5,648,701 A * | 7/1997 | Hooke et al. ........... 315/111.21 |
| 5,818,581 A | 10/1998 | Kurosawa et al. |
| 6,329,757 B1 | 12/2001 | Morrisroe et al. |

OTHER PUBLICATIONS

Rod W. Boswell et al. "Helicons-The Early Years" Dec. 6, 1997, pp. 1229-1245.
Examiner's first report, Australian. Apr. 11, 2006.

* cited by examiner

*Primary Examiner*—F. L. Evans
(74) *Attorney, Agent, or Firm*—St. Onge Steward Johnston & Reens LLC

(57) ABSTRACT

In a method of spectroscopically analyzing a sample, a plasma is generated. A magnetic field is generated by a magnetic dipole wherein the plasma is confined within the magnetic field. Sample atoms are introduced into the plasma wherein energized atoms of the sample are confined. The spectral composition or mass-to-charge ratio of the energized sample atoms is analyzed. In a spectroscopic system a magnetic dipole has an associated magnetic field. A plasma is confined within the magnetic field and a sample of energized atoms introduced into the plasma. A spectrometer analyzes the energized atoms for the mass-to-charge ratio or for their spectral composition.

22 Claims, 8 Drawing Sheets

ICP-OES AND ICP-MS INDUCTION CURRENT

RELATED APPLICATIONS

This application claims the benefit of U.S. provisional patent application No. 60/432,963 filed Dec. 12, 2002 which is incorporated herein by reference thereto as if set forth at length.

FIELD OF THE INVENTION

This invention relates to a method and apparatus for spectroscopically analyzing a material sample in a plasma.

BACKGROUND OF THE INVENTION

Conventional Inductively Coupled Plasma-Optical Emission Spectroscopy ICP-OES and Inductively Coupled Plasma-Atomic Emission Spectroscopy ICP-MS systems typically utilize a solenoid receptive of an RF electrical current for confining a plasma and material sample in an associated magnetic field for analysis. However, such a device generates an uneven magnetic field over the length of the interior of the solenoid due to the helical configuration of the solenoid. This results in an uneven temperature distribution within the plasma affecting sample excitation and the trajectory of ions in the plasma. In addition, the solenoid is a single element, which lacks flexibility in controlling the associated magnetic field and the plasma/sample excitation.

SUMMARY OF THE INVENTION

In a method of spectroscopically analyzing a sample, a plasma is generated. A magnetic field is generated by a magnetic dipole wherein the plasma is confined within the magnetic field. Atoms of a material sample are introduced into the plasma wherein energized atoms of the sample are at least temporarily confined. The spectral or mass content of the energized sample atoms are analyzed.

In a spectroscopic system a magnetic dipole has an associated magnetic field. A plasma is confined within the magnetic field and a material sample of atoms is introduced into the plasma. A spectrometer analyzes the excited atoms for their mass-to-charge ratio or for their emission spectra.

DETAILED DESCRIPTION OF THE DRAWINGS

Figure 1:
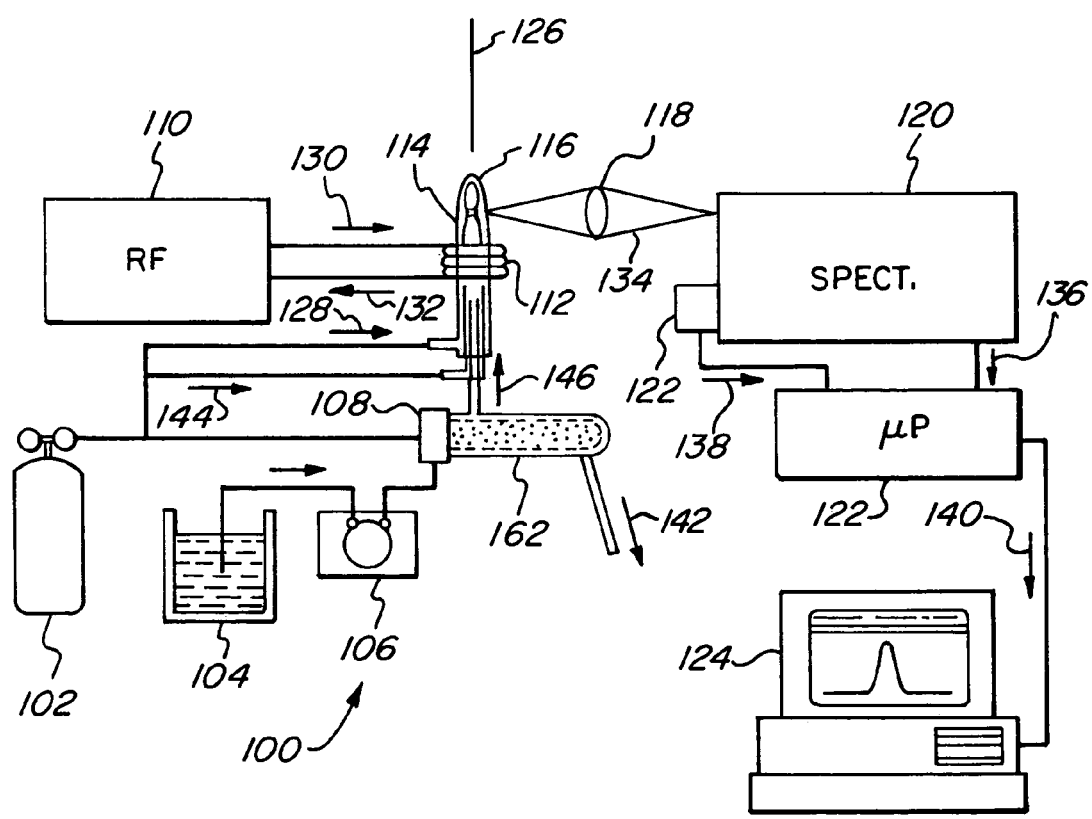
FIG. 1 is schematic diagram of an Inductively Coupled Plasma-Optical Emission Spectroscopy (ICP-OES) system.

FIG. 1 shows a schematic diagram of an Inductively Coupled Plasma-Optical Emission Spectroscopy (ICP-OES) system at 100. The ICP-OES 100 generally comprises a system for directing a carrier gas 102 to a torch 114 whereat the carrier gas 102 is ionized to form a hot plasma 116 (5,000–10,000 K). The plasma 116 comprises a preheating zone 190, an induction zone 192, an initial radiation zone 194, an analytic zone 196 and a plasma tail 198. An atomized sample 104 is also directed to the plasma 116 through a pump 106, nebulizer 108 and spray chamber 162. A radio frequency (RF) power source 110 provides RF electrical power to the plasma 116 by way of a load coil 112.

Figure 2:
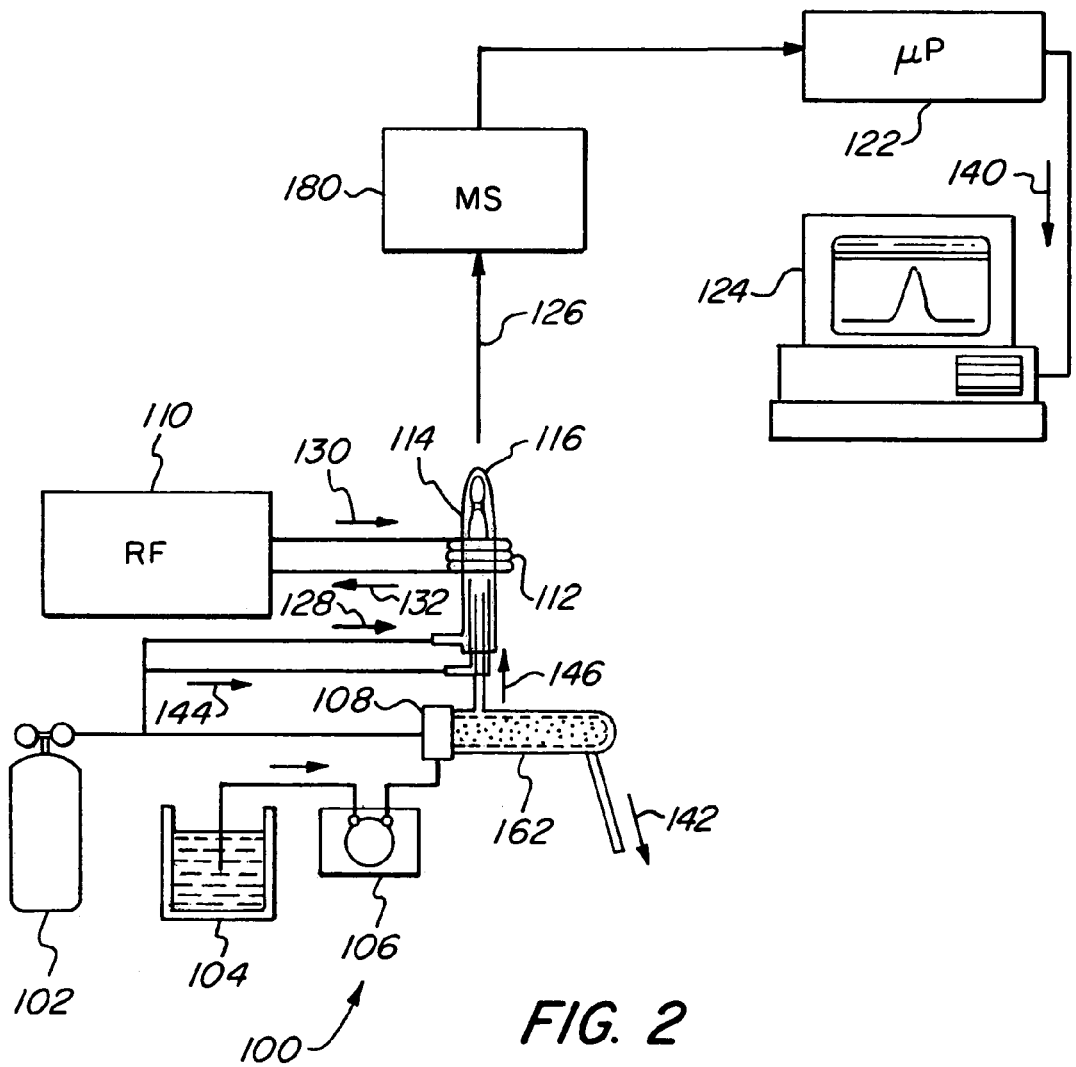
FIG. 2 is schematic diagram of an Inductively Coupled Plasma-Mass Spectroscopy (ICP-MS) system.

While in the plasma 116 excited sample atoms 104 give off light 134 as they decay to a lower state. The light 134 is collected by collection optics 118 and directed to a spectrometer 120 where it is spectrally resolved. A detector 122 detects the spectrally resolved light 134 and provides a signal 138, 140 to a microprocessor 122 and computer network 124 for analysis. In FIG. 1 it is seen that the viewing of the plasma 116 is from a direction at a right angle to the plasma 116. However, it will be understood from FIG. 1 that the viewing of the plasma 116 may also be performed from a direction along the axis 126. It will also be understood that the Inductively Coupled Plasma Spectroscopy performed herein may also be performed with a mass spectrometer (MS) 180 such as a quadrupole mass analyzer in an Inductively Coupled Plasma-Mass Spectroscopy (ICP-MS) system at 100 as seen in FIG. 2. The RF power source 110 operates generally in the range of 10 to 100 MHz, particularly 20–50 MHz, e.g., 27–40 MHz.

Figure 3:
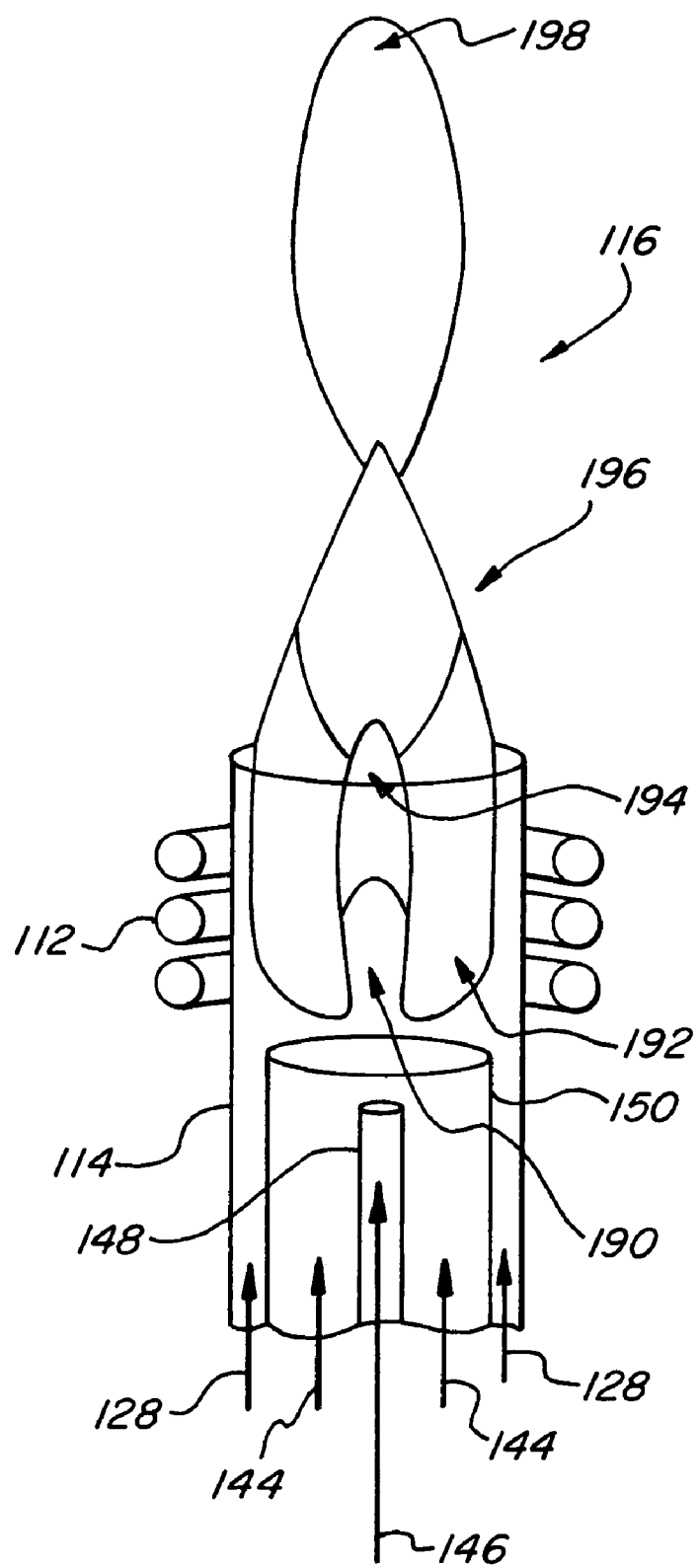
FIG. 3 is a diagram of an ICP torch and a plasma.

FIG. 3 shows a more detailed rendition of the plasma 116 of FIGS. 1 and 2. The torch 114 includes three concentric tubes 114, 150, 148. The innermost tube 148, provides atomized flow 146 of the sample into the plasma 116. The middle tube 150, provides auxiliary gas flow 144 to the plasma 116. The outermost tube 114, provides carrier gas flow 128 for sustaining the plasma. The carrier gas flow 128 is directed to the plasma 116 in an laminar flow about the middle tube 150. The auxiliary gas flow 144 is directed to the plasma 116 within the middle tube 150 and the atomized sample flow 146 is directed to the plasma 116 from the spray chamber 162 along the innermost tube 148. The RF current 130, 132 in the load coil 112 forms a magnetic field within the load coil 112 so as to confine the plasma 116 therein.

Figure 4:
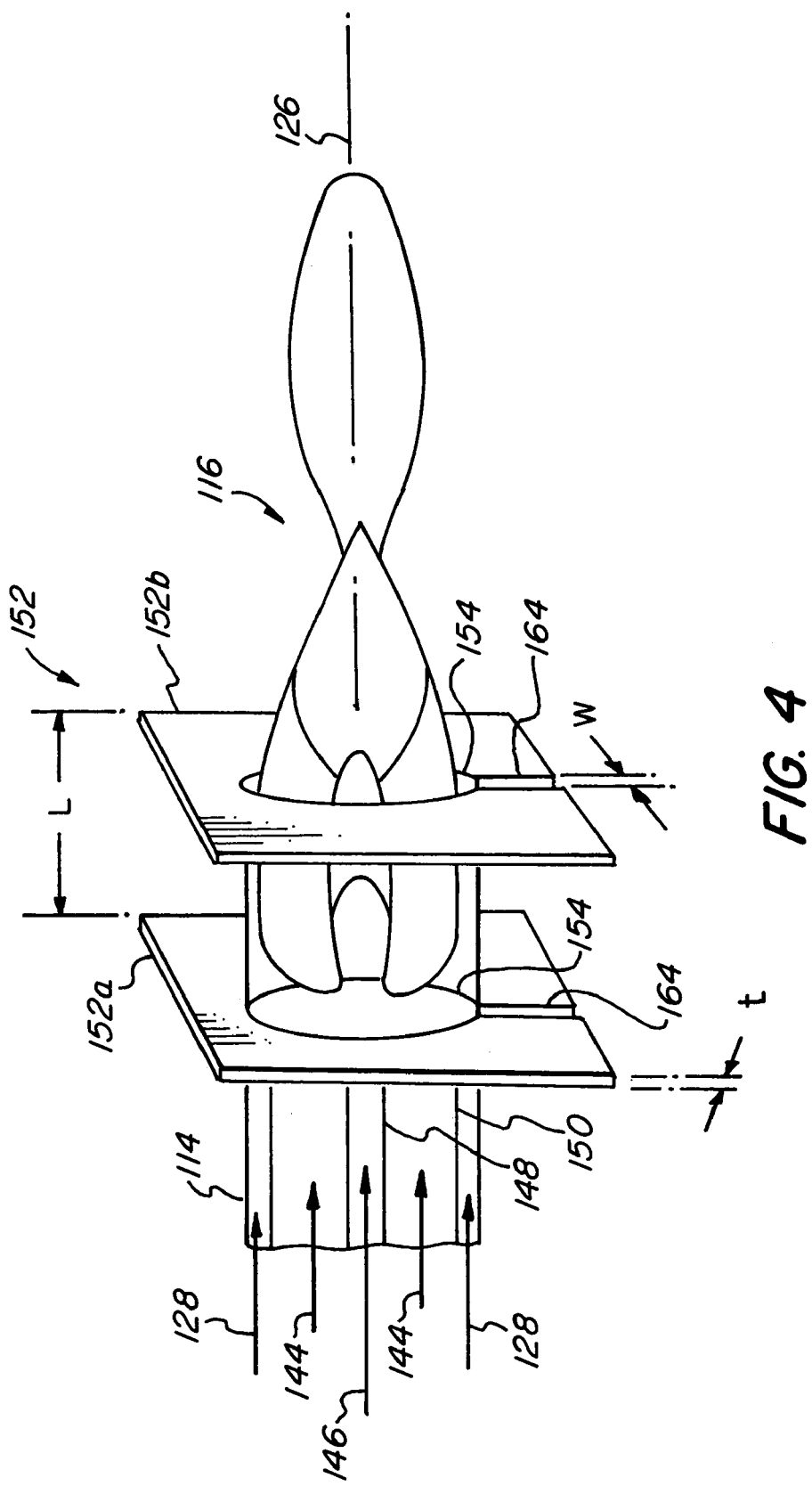
FIG. 4 is a side view of two electrodes of the invention and an ICP torch and a plasma.

FIGS. 4–11 show various configurations of an electrode 152, 156, 158. In FIG. 4 the electrode 152 comprises two parallel plates 152$a$, 152$b$ positioned at a distance 'L' from one another. The parallel plates 152$a$, 152$b$ each include an aperture 154 through which the torch 114 is positioned such that the torch 114, the innermost tube 148, the middle tube 150 and the aperture 154 are aligned along an axis 126. The parallel plates 152$a$, 152$b$ have a thickness of 't.' The aperture 154 of the electrode 152 also includes a slot 164, of width 'w' such that the aperture 154 is in communication with its surroundings.

Figure 5:
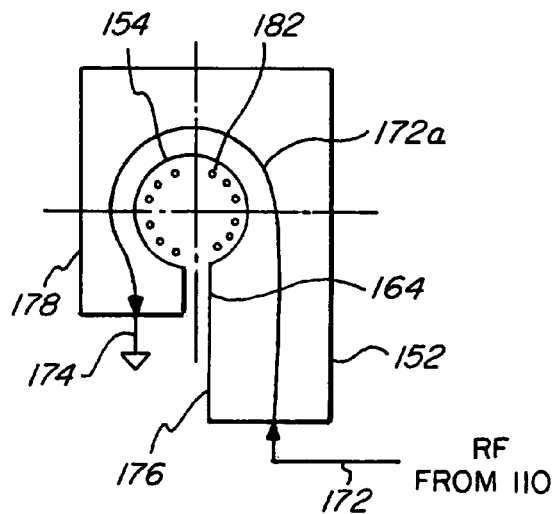
FIG. 5 is a front view of an electrode for controlling a plasma, the electrode including an aperture.
Figure 7:
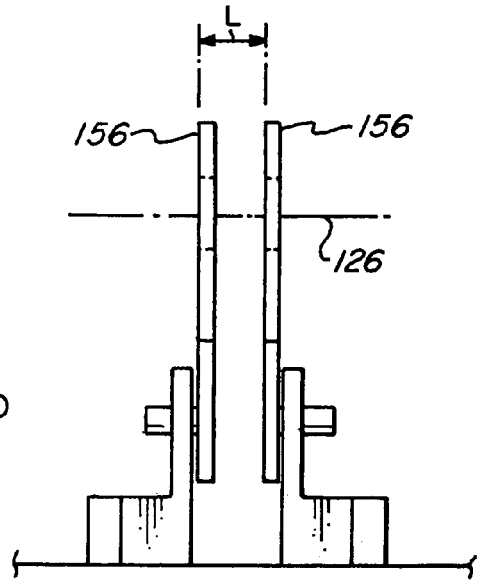
FIG. 7 is a side view of the electrodes of FIG. 6.
Figure 6:
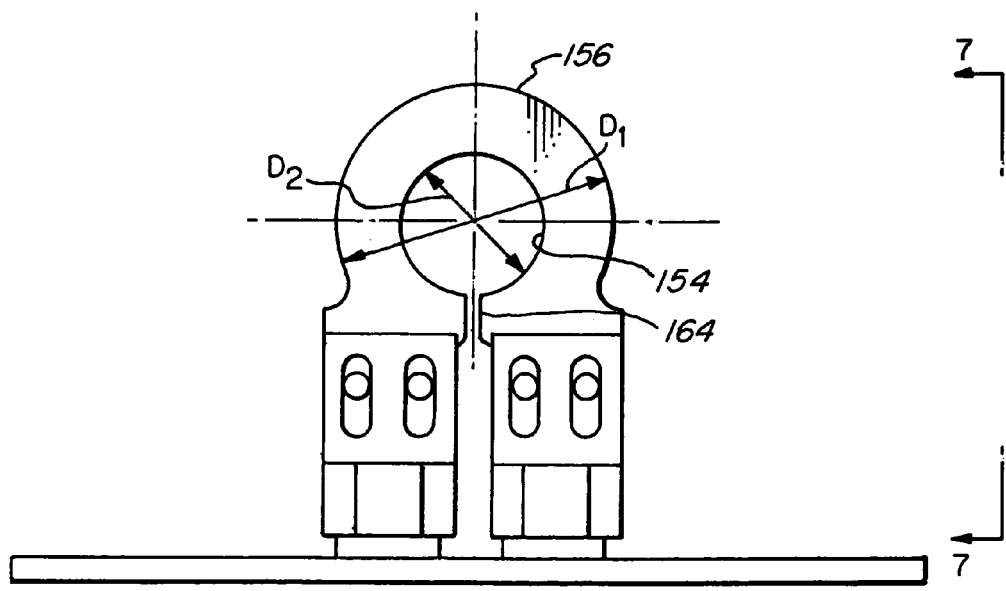
FIG. 6 is a front view of an electrode for controlling a plasma, the electrode including an aperture.
Figure 8:
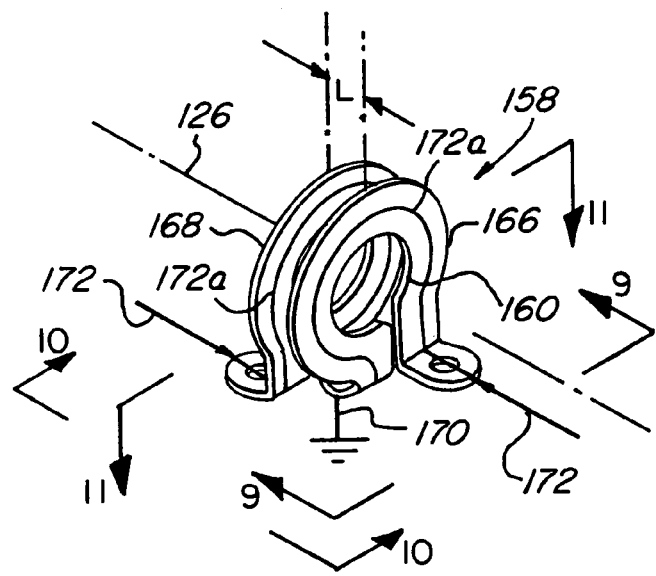
FIG. 8 is a three dimensional view of a single piece electrode of the invention.
Figure 9:
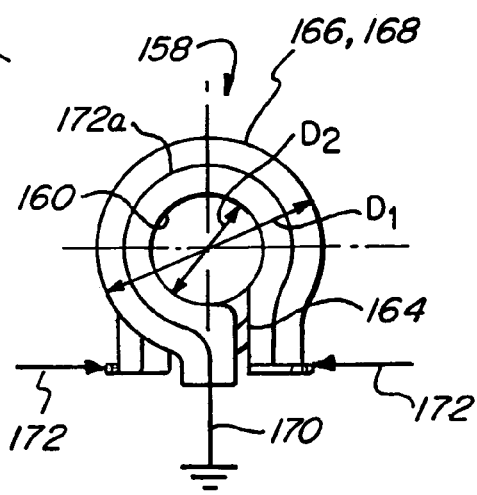
FIG. 9 is a front view of the single piece electrode of FIG. 8.
Figure 10:
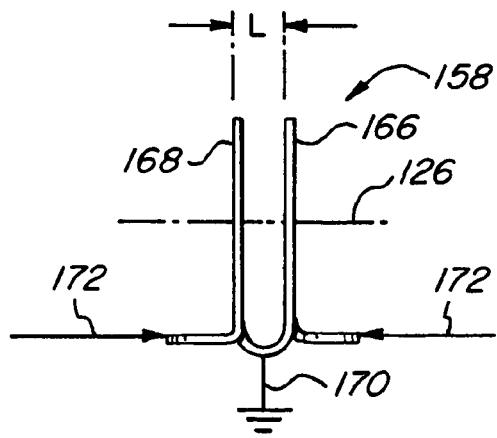
FIG. 10 is a side view of the single piece electrode of FIG. 8.
Figure 11:
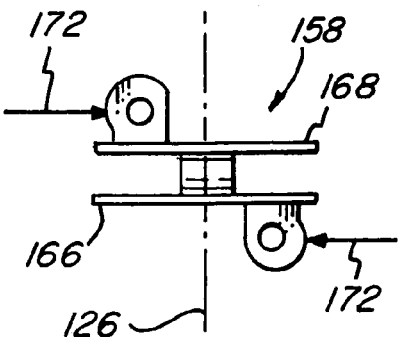
FIG. 11 is a top view of the single piece electrode of FIG. 8.
Figure 12:
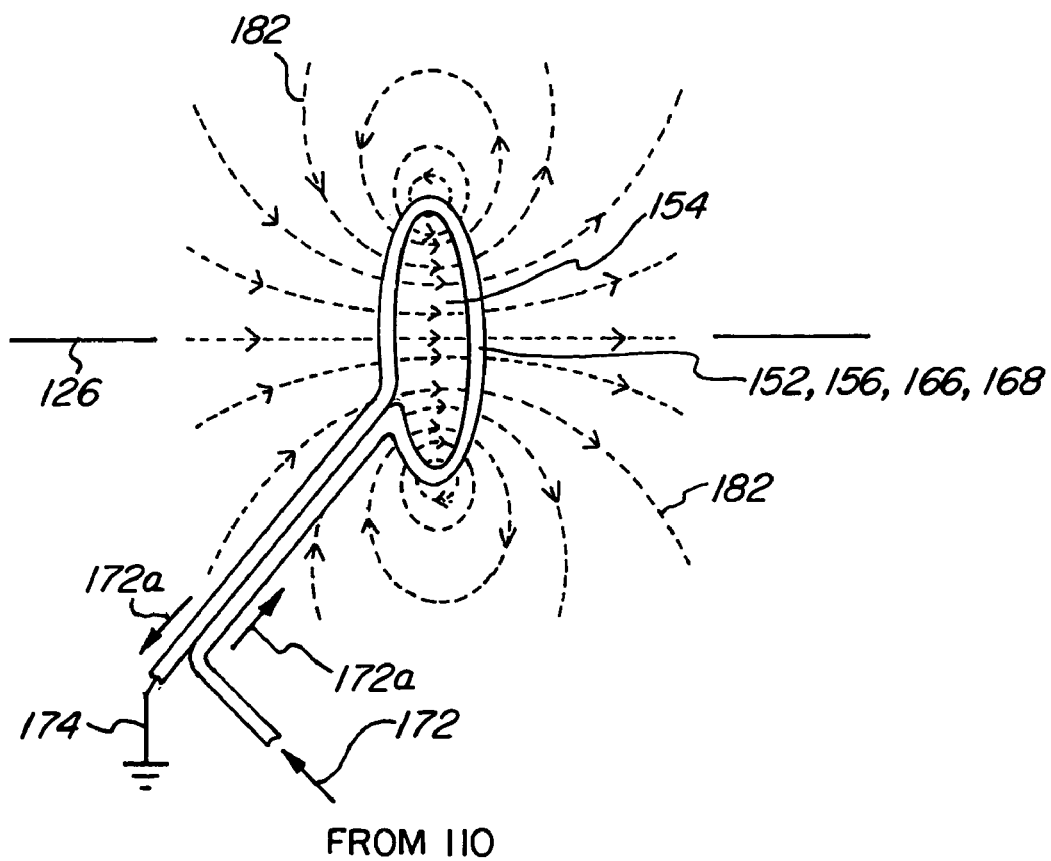
FIG. 12 is a three dimensional view of a magnetic field generated from a loop current.
Figure 13:
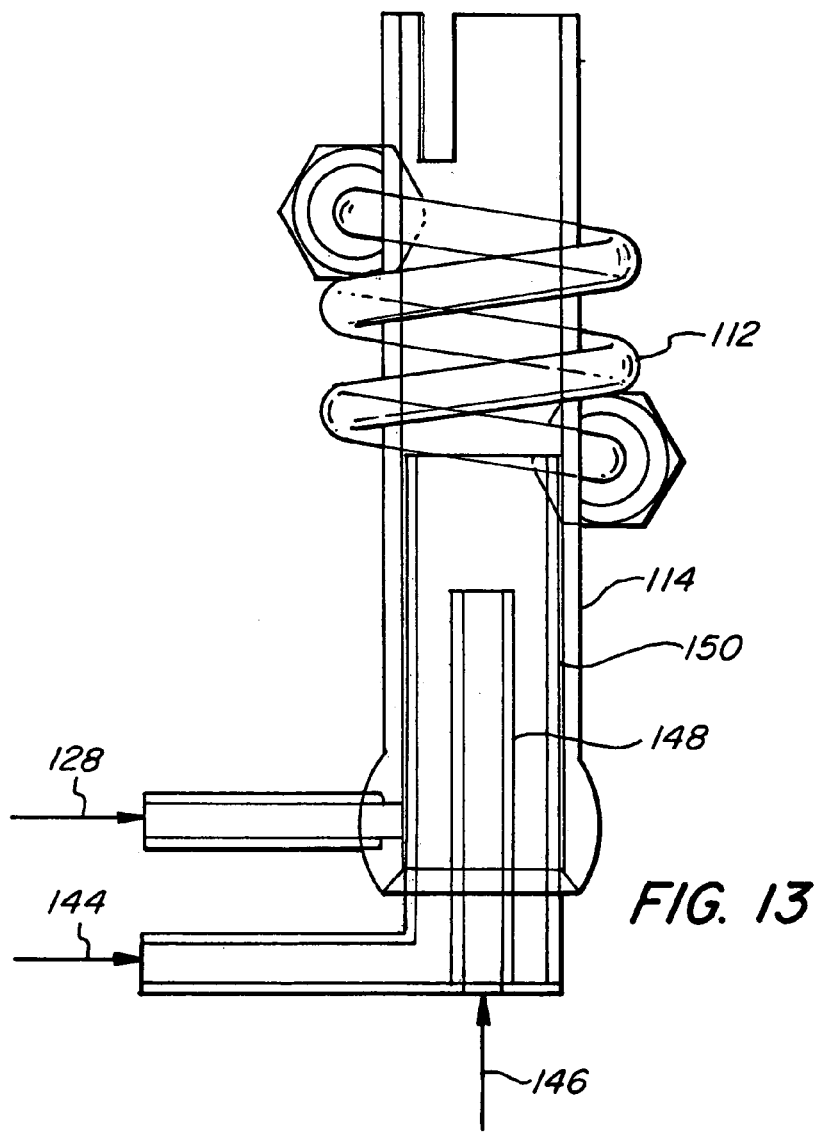
FIG. 13 is a diagram of an ICP torch showing the helical nature of a solenoid.

As seen in FIGS. 4 and 5, the electrode 152 is generally comprised of a square or rectangular planar shape, though it may be a wire as seen in FIG. 12. In FIG. 5 it will be appreciated that the RF current supplied to the planar electrode comprises a planar current loop 172a generating a toroidal magnetic field 182 through the aperture 154 (FIG. 12). In FIGS. 6 and 7 the electrode 156 is of a rounded nature having an outside diameter of $D_1$ and inside aperture diameter of $D_2$. The electrodes 152, 156 of FIGS. 4–7 are distinct elements which are supplied independently with RF electrical current 172 of opposite polarity. One part 176 of the electrode 152 is supplied with the RF power while a second part 178 of the electrode 152 is tied to a ground 174. Thus, during arc ignition of the plasma 116, if the ignition arc makes contact with electrode 152, any unwanted electric currents set up in the electrode 152 will be directed to the ground point 174 and not through to the RF power supply 110. The RF power and frequency supplied to each electrode 152 can be independently controlled and varied for optimum performance. For instance, each electrode 152 can be driven at a different frequency in order to optimize the plasma emission and excitation. In addition, one electrode can be operated in a continuous power mode while the other electrode can be modulated (e.g.; pulsed or gated). Furthermore, the distance, 'L', between the electrodes 152 can be adjusted since the electrodes 152 are not connected to one another; thus adjusting the power distribution within the plasma 116. Yet further, the diameter, $D_2$, of the aperture 154 can be independently adjusted in order to adjust the coupling characteristics between the RF power supply 110 and the plasma 116. In FIGS. 8–11 the electrode 158 is shown as a single element having two electrodes 166, 168 connected to a common electrical ground 170.

Figure 14:
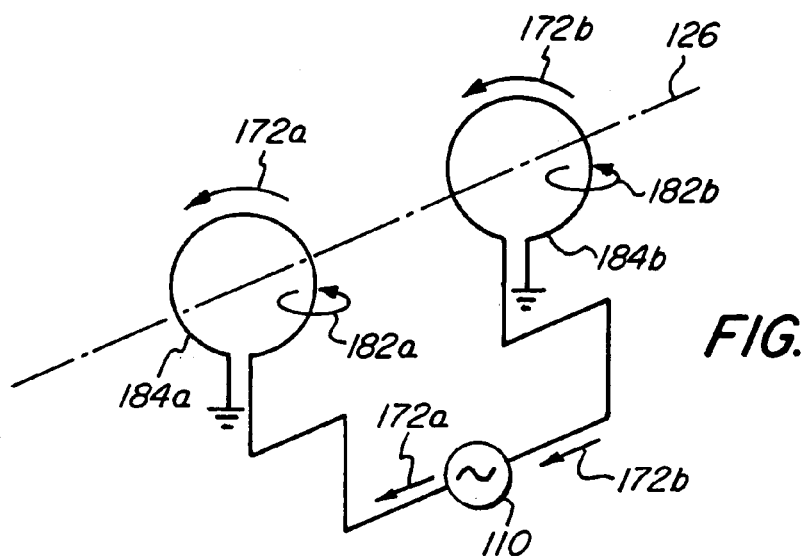
FIG. 14 is a diagram of a plurality of loop currents driven by a single RF power source during alternating half cycles of a sinusoidally alternating current.

In FIG. 14 a plurality of loop currents 184a, 184b is shown generated from a single RF electric current source 110. The loop currents 184a, 184b are oriented with respect to one another in such a manner that the alternating electric current 172a in a first loop current 184a flows in a direction opposite to that of the alternating electric current 172b in a second loop current 184b during alternating half cycles of a sinusoidally alternating current. This allows for the plurality of loop currents 184a, 184b to be driven from a single power source 110 so as to generate magnetic fields 182a, 182b having the same spatial orientation.

While the invention has been described above in detail with reference to specific embodiments, various changes and modifications which fall within the spirit of the invention and the scope of the claims will become apparent to those skilled in the art. Therefore, the invention is intended to be limited only by the appended claims and their equivalents.

Thus, based upon the foregoing description, a method and apparatus for spectroscopically analyzing a sample is disclosed. The method comprises generating a plasma; generating a magnetic field by a magnetic dipole wherein the plasma is confined within the magnetic field; introducing sample atoms into the plasma wherein excited sample atoms are confined; and analyzing the spectral or mass content of the excited sample atoms.

Furthermore, a spectroscopic system comprises a magnetic dipole having an associated magnetic field; a plasma confined within the magnetic field; a sample of excited atoms introduced within the plasma; and a spectrometer for analyzing the spectral or mass content of the excited sample atoms.

What is claimed is:

1. A method of spectroscopically analyzing a material sample, the method comprising:
   generating a plasma;
   generating a loop current so as to generate a magnetic field, wherein the plasma is confined within the magnetic field;
   introducing atoms of the material sample into the plasma wherein excited sample atoms are confined; and
   analyzing characteristic features of the excited sample atoms.

2. The method as set forth in claim 1 wherein generating a loop current comprises generating a sinusoidally alternating electric current.

3. The method as set forth in claim 2 wherein generating a sinusoidally alternating electric current comprises generating a radio frequency electric current.

4. The method as set forth in claim 1 wherein analyzing characteristic features of the excited sample atoms comprises analyzing the spectral composition or mass-to-charge ratio of the excited sample atoms.

5. The method as set forth in claim 1 further comprising electrically grounding the loop current.

6. The method as set forth in claim 2 wherein generating a loop current comprises generating a planar loop current.

7. The method as set forth in claim 6 wherein the loop defines an aperture.

8. The method as set forth in claim 6 wherein generating a loop current comprises generating a plurality of loop currents.

9. The method as set forth in claim 8 wherein generating a plurality of loop currents comprises generating a plurality of parallel or antiparallel loop currents separated by a prescribed distance.

10. The method as set forth in claim 9 wherein the alternating electric current in a first loop current flows in a direction opposite to that of the alternating electric current in a second loop current during alternating half cycles of the sinusoidally alternating current.

11. The method as set forth in claim 7 further comprising adjusting an area of the aperture.

12. The method as set forth in claim 9 further comprising adjusting the prescribed distance.

13. A spectroscopic system comprising:
   an electric current source for generating a loop current, said loop current having an associated magnetic field;
   a plasma gas generator for generating a plasma at least in part by a carrier gas flow introduced within the magnetic field via a carrier gas conduit said plasma confined within the magnetic field;
   a material sample conduit for introducing a material sample into the plasma, the atoms of said material sample being excited within the plasma and;
   a spectrometer for analyzing characteristic features the excited atoms.

14. The spectroscopic system as set forth in claim 13 further comprising an electric power generator for generating the loop current.

15. The spectroscopic system as set forth in claim 14 wherein the loop current is a sinusoidally alternating electric current.

16. The spectroscopic system as set forth in claim 15 wherein the sinusoidally alternating electric current is a radio frequency current.

17. The spectroscopic system as set forth in claim 13 wherein the loop current is a planar current.

18. The spectroscopic system as set forth in claim 13 wherein the loop current defines an aperture.

19. The spectroscopic system as set forth in claim 13 wherein the loop current comprises a plate.

20. The spectroscopic system as set forth in claim 13 wherein the loop current comprises a plurality of plates.

21. The spectroscopic system as set forth in claim 20 wherein the plurality of plates are parallel.

22. A spectroscopic system comprising:
- an electric current source for generating a loop current, the loop current having an associated magnetic field;
- a carrier gas conduit for introducing a carrier gas within the magnetic field, said carrier gas for sustaining a plasma generated within the magnetic field;
- a material sample conduit for introducing the atomized material sample into the plasma, and;
- a spectrometer positioned in the vicinity of the plasma for analyzing characteristic features of excited atoms of the material sample.

* * * * *